US00PP14236P29

(12) United States Plant Patent
Minazzoli

(10) Patent No.: US PP14,236 P2
(45) Date of Patent: Oct. 14, 2003

(54) WALNUT TREE NAMED 'FREDRICK'

(50) Latin Name: *Juglans regia*
Varietal Denomination: 'Fredrick'

(76) Inventor: Fred Minazzoli, 5051 N. Boggiano Rd., Stockton, CA (US) 95215

( * ) Notice: Subject to any disclaimer, the term of this patent is extended or adjusted under 35 U.S.C. 154(b) by 0 days.

(21) Appl. No.: 10/289,716

(22) Filed: Nov. 6, 2002

(51) Int. Cl.[7] ..... A01H 5/00
(52) U.S. Cl. ..... Plt./154

(58) Field of Search ..... Plt./154

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of walnut tree denominated as 'FREDRICK' is described and which is somewhat remotely similar to the 'Payne' walnut tree (unpatented), but which is distinguished therefrom by producing a crop which is mature for harvesting and shipment approximately 7 days after the 'Payne' walnut tree under the ecological conditions prevailing near Stockton, Calif.

1 Drawing Sheet

BACKGROUND OF THE NEW VARIETY

The present invention relates to a new and distinct variety of walnut tree *Juglans regia* which has been denominated varietally as 'FREDRICK,' and more particularly to such a walnut tree which has a harvest date approximately one week later than the walnut tree variety 'Payne' (unpatented) and which further produces a nut which is ovate in shape and which has a relatively smooth surface texture and light colored shell, and which is suitable for in-shell use.

It has long been recognized as desirable to provide walnut trees bearing crops which are ripe for commercial harvesting and shipment and which are later in time relative to other well known and commercially acceptable varieties. The present variety, 'FREDRICK' produces a nut, which is similar, in some respects, to common walnut tree varieties such as 'Payne' (unpatented); 'Chandler' (U.S. Plant Pat. No. 4,388) and 'Hartley' (unpatented). The tree of the present variety is noteworthy inasmuch as the variety 'FREDRICK' produces a heavy crop which is considered to be greater than or equal than that produced by the walnut tree 'Payne' at the same geographical location. Still further, the present variety of walnut tree matures for harvesting and shipment approximately September 14 under the ecological conditions prevailing in the vicinity of Stockton, Calif.

ORIGIN ASEXUAL REPRODUCTION OF THE NEW VARIETY

The present variety of walnut tree was discovered as an open pollinated seedling of the walnut cultivar 'Payne' (unpatented), and which was growing within the cultivated area of the inventor's orchard which is located at 6000 North Cox Road, Linden, Calif. 95236. The inventor first discovered the novel walnut tree in a cultivated, existing mature walnut orchard which contained the walnut cultivars 'Payne,' 'Hartley,' and 'Serr' (all unpatented) during routine orchard operations in 1975. The inventor subsequently marked the new open pollinated seedling for subsequent observation.

After several seasons of observation, the first asexual reproduction of the newly discovered variety of walnut tree occurred in 1980 when the inventor removed wood from the open pollinated seedling and grafted it into 'Paradox' (unpatented) root stock. This grafted root stock has been subsequently observed through several growing years, and the inventor has confirmed that the grafted tree has identical characteristics to that observed in the original open pollinated seedling.

SUMMARY OF THE NEW VARIETY

The walnut tree 'FREDRICK' is characterized principally as to novelty by producing a relatively heavy yield nut crop which is ripe for harvesting and shipment about September 14$^{th}$ under the ecological conditions prevailing in Stockton, Calif. This date of harvesting is approximately one week after the walnut variety 'Payne' at the same geographical location. As compared to the nut produced by the 'Payne'walnut tree, the present variety produces a nut which is larger in size. Further, the new variety appears more vigorous than the 'Payne' walnut tree at the same geographic location.

BRIEF DESCRIPTION OF THE DRAWINGS

The accompanying drawing is an illustration by composite photographic reproduction of a mature walnut tree of the new variety; a portion of a branch of the new variety showing a mature crop ready for harvesting and which further shows the dorsal and ventral coloration of the leaves; and several views of the nuts produced by the present variety of walnut tree.

DETAILED DESCRIPTION

Referring more particularly to the specific botanical details of this new and distinct variety of walnut tree, the following has been observed under the ecological conditions prevailing at the inventor's orchard which is located at 6000 North Cox Road, Linden, Calif. 95236. All major color code designations are made by reference to the ISCC-NBS Centroid Color Charts provided by the National Bureau of Standards and further supplemented by way of the Nickerson Color Fan which is distributed by the American Horticultural Society and which was originally published by Munsell Color Co. in 1957. Common color names are also used occasionally.

Tree:

*Generally.*—The description which follows relates to the tree which was originally grafted onto 'Paradox' (unpatented) root stock as noted above.

*Size and maturity.*—Approximately 30 to about 35 feet (9 to about 11 meters) in height when measured at 10 years of age. This is quite similar to the walnut cultivar 'Payne' when grown under similar ecological conditions prevailing near Stockton, Calif. It should be understood that the 'Payne' walnut tree is considered to be a medium sized tree. It is a very old variety and it has been considered noteworthy through the years for it's very high productivity. The nuts produced by the 'Payne' walnut tree are considered medium to small. The seal on the nuts is considered good and the rate of crackout is about 48%. The nuts average approximately 48% kernel. The 'Payne' walnut tree is also considered to be an early blooming and early harvest variety.

*Vigor.*—Considered moderate as compared to other comparable varieties. In comparison to the 'Payne' walnut tree, the present variety 'FREDRICK' is considered to be more vigorous.

*Regularity of bearing.*—Annually.

Trunk:

*Size at full maturity.*—Approximately 7 to 12 inches (18 to about 30 centimeters) in diameter when measured at a distance of about 4.5 feet above ground level.

*Surface texture.*—Generally — The trunks of both young and older trees have relatively smooth surface textures.

*Color of bark.*—Generally — Mature bark is a light creamy, grey color which resembles, to some degree, the bark displayed by the 'Chandler' walnut tree. The color of younger branches are darker, and include much more brown coloration (5.5 YR 3.5/1.8). Mature trees have a light gray olive bark color (7.8 Y 5.5/2.5).

*Lenticels.*—Numbers — The variety 'FREDRICK' generally has 9 lenticels per square inch of bark surface area.

*Lenticel size.*—The lenticels have an oval shape and dimensions of approximately 0.5 inches by 0.1 inches.

*Lenticel color.*—Gray brown, 5.5 YR 3.5/1.8.

Branches:

*Size.*—Branches up to 8 inches in diameter can be found.

*Form.*—Mature limbs are considered to be moderately upright.

*Surface texture.*—Mature branches — Smooth.

*Surface texture.*—Immature branches — Smooth.

*Branch color.*—1 year or older — gray brown, 5.5 YR 3.5/1.8.

*Branch color.*—Immature branches — strong yellow-green, 2.5 GY 6/8.

*Lenticels.*—Numbers — Approximately 30 lenticels per square inch may be found on the branches.

*Lenticel size.*—Approximately 0.04 inches by about 0.06 inches.

*Branching habit.*—Considered moderately upright to spreading. New growth on trees is considered to be weepy like the 'Vina' walnut tree (unpatented), and further having a moderate amount of narrow forking. The 'Vina' walnut tree is harvested early to mid-season. It also produces a medium size and pointed nut. It's tree size is considered small to medium and it is moderately vigorous and considered to be highly productive.

*Observed crotch angles.*—Variable, from about 50° to 70° as measured from the horizontal. This characteristic is not distinctive of this particular variety, however.

Leaves:

*Foliage abundance.*—The foliage of the subject variety is abundant and covers the nuts in the interior of the tree canopy. The nuts are generally exposed on the branch tip, especially if a heavy crop is produced.

*Foliage arrangement.*—Evenly distributed in the canopy.

*Size.*—Length — The variety has compound leaves which have a length dimension of about 14 to 20 inches (31–51 centimeters). Typical fully, light-exposed, mature leaves have a length dimension of about 18 inches (46 centimeters).

*Leaf width.*—About 12 to 18 inches (30–38 centimeters). Typically, the average width of the leaves is approximately 14 inches (36 centimeters).

*Leaf shape.*—Generally — Pinnately compound.

*Number of leaflets.*—Typically, 7 leaflets per leaf.

*Leaflet length.*—About 5 to about 8 inches (13 to about 20 centimeters).

*Leaflet width.*—About 1.5 to about 3 inches (4 to about 8 centimeters).

*Leaflet shape.*—Considered broadly elliptical.

*Leaflet thickness.*—About 0.015 to about 0.020 inches (0.4 to about 0.5 millimeters).

*Leaflet texture.*—Generally smooth.

*Leaflet margins.*—Entire, that is having a smooth, non-serrated edge.

*Leaf color.*—Immature leaves — Upper surface, moderate olive green, (5 GY 4/3). Lower surface — Moderate olive green (2.5 GY 4/3).

*Color.*—Mature Leaves — Upper surface, greyish-olive green (5 GY 3/2).

*Color.*—Mature Leaves — Lower Surface — Moderate olive green (5 GY 4/3).

*Leaf vein.*—Color — Brilliant yellow-green, (2.5 GY 7/8).

*Leaf vein thickness.*—About 0.5 inches (1.3 millimeters).

*Leafing dates.*—Bud break — About 2 days after the 'Payne' walnut tree, approximately March 20$^{th}$ under the ecological conditions prevailing in the vicinity of Stockton, Calif.

*Petiole.*—Length — About 9 to 13 inches (23–33 centimeters). The typical distance from the base of the petiole to the first leaflet is approximately 3 inches (7.5 centimeters).

*Petiole thickness.*—About 0.1 inches (2.5 millimeters) when measured about mid leaf.

*Petiole color.*—Yellow-Green, (2.5 GY 6/8).

Flowers:

*Date of female bloom.*—The female bloom is very close to that seen with respect to the 'Payne' variety of walnut tree, and about one day later. Date of first female bloom is about March 29$^{th}$. Date of peak female bloom is about April 1$^{st}$. Further, the date of last female bloom is about April 5$^{th}$.

*Amount of female bloom.*—Generally — Considered moderately heavy. However, this bloom amount is less than that seen on the 'Payne' walnut trees which are growing in the same geographical vicinity.

*Date of first male bloom.*—About March 24$^{th}$. Date of peak male bloom is about March 28$^{th}$. Date of last male bloom is about April 1$^{st}$.

*Amount of male bloom.*—Generally — Considered moderate and less than what is seen on the 'Payne' walnut trees which are growing in the same geographical vicinity.

*Bloom habit.*—Generally — Considered terminal bearing and protandrous.

*Inflourescences.*—Precocity — Not considered particularly precocious. This characteristic is typical of terminal bearing trees. In this regard, bearing is primarily seen on mature branches.

*Number of flowers per bearing site.*—About 1 to 3 and generally 2 flowers per inflourescence.

*General appearance of the flowers.*—The variety 'FREDRICK' produces flowers which appear typical for the species in both color and shape.

*Female flower color.*—As a general matter, the floral surface has a yellow-green color (5 GY 6/8), and the stigma tips and upper surface are tinged with a reddish-orange color (7.5 R 6/12).

*Male flower color.*—Yellow-green (5 GY 6/8).

*Floral fragrance.*—Not particularly distinctive, but rather is considered typical of this species and is generally not noticeably different from the foliage fragrance.

*Flower size.*—Male — Average for the species, approximately 3 to about 5 inches (7 to about 13 centimeters) in length; and about 0.6 to about 0.7 inches (15 to about 18 millimeters) in diameter.

*Flower size.*—Female — Average for the species, about 0.15 to about 0.16 inches, (4 to about 6 millimeters) in diameter; and about 0.3 to about 0.5 inches (8 to about 12 millimeters) in length. The distance across the fully extended stigmas is about 0.2 to about 0.4 inches (5 to about 10 millimeters).

*Crop.*—Productivity — The present variety 'FREDRICK' is considered to produce a heavy nut yield. This nut yield is considered better than the 'Payne' variety of walnut trees growing in the same geographical area.

*Harvesting time.*—The present variety is harvested approximately one week after the 'Payne' variety walnut tree at the same geographical location. The date of harvest is about September 14$^{th}$ under the ecological conditions prevailing in the vicinity of Stockton, Calif.

*Distribution of nuts on the tree.*—As a general matter, nuts are well distributed in the canopy and most of the yield of the nuts is in the mature portions of the canopy.

*Bearing habits.*—Considered terminal.

*Evenness of maturity.*—Uniform. In this regard, most hulls loosen within about a one week period.

*Nut quality.*—As a general matter, the nuts produced by the subject variety of walnut tree are uniform in size, and shape, and have intact shells with closed seals. The nuts break cleanly from the hulls and have an attractive exterior appearance and have a shape similar to that produced by the 'Payne' variety of walnut tree.

*Hull.*—Texture — Smooth and as a general matter, non-hairy by mid-summer.

*Hull form.*—Appearing somewhat similar to the 'Payne' variety of walnut tree, but not as pointed as the hull produced by the 'Vina' or 'Hartley' walnut trees (both unpatented). In this regard, the 'Hartley' walnut tree has been, for some period of time, the number one walnut tree in California. In this regard, the 'Hartley' walnut tree produces what is considered to be a large thin shelled well sealed nut. The 'Hartley' walnut tree is considered to be a medium to large tree, and it requires a late blooming pollenizer in order to set a crop.

*Hull thickness.*—About 0.17 to about 0.20 inches (4.3 to about 5.0 millimeters) immediately prior to harvest.

*Hull color.*—A moderate yellow-green, (5 GY 5/6).

*Dehiscence.*—The hulls dehisce and separate from the shell cleanly. Some cracking on the outer surface is visible at hull loosening. This is typical of most common walnut cultivars.

*Splitting tendency.*—A cracking pattern appears on the outer fractured hull. In this regard, an alligator-skinlike pattern emerges which appears to be not much different from that seen on the 'Payne' walnut tree variety.

*Nut.*—Shape — Considered ovate and similar to the 'Payne' variety of walnut tree, but appearing slightly more pointed. In this regard the shape is somewhat intermediate between what is produced by the 'Payne' and 'Hartley' walnut tree varieties.

*Nut size.*—Length — About 1.52 inches (38.7 millimeters).

*Nut width.*—About 1.32 inches (about 33.5 millimeters).

*Nut weight.*—Generally — About 0.04 ounces (11.4 grams).

*Shell.*—Color — Light brown, (2 Y 5/6). This color appears to be average for the species.

*Shell thickness.*—About 0.055 inches (about 1.4 millimeters).

*Shell texture.*—Moderate to smooth. It appears somewhat slightly smoother than that produced by the 'Payne' variety of walnut tree.

*Shell seal.*—The seal appears to be of moderate strength and similar to that produced by 'Chandler' walnut tree (U.S. Plant Pat. No. 4,388).

*Shell strength.*—Considered moderate.

*Kernel.*—Weight — About 0.23 ounces (6.6 grams). This is somewhat similar to that produced by the 'Payne' variety of a walnut tree.

*Percentage of kernel relative to the nut.*—About 54%.

*Kernel color.*—Considered excellent. In this regard, the kernels of the subject variety scored mostly in the "extra light" category of the U.S. Department of Agriculture Standards for grades of shelled walnuts as determined using the standard walnut color chart for kernels published by the dried fruit association of California. Yet further the kernel sample provided from the subject variety scored about 53.9 on the Relative Light Index as used by Diamond Walnut of Stockton, Calif. The kernels of the subject variety have a shiny kernel surface similar to that produced by 'Chandler' variety of walnut trees. Occasionally, a few dark veins appear.

*Commercial use.*—The present variety harvests early in the season and further has a shell appearance and strength suitable for in-shell use. Still further, the present variety has an excellent kernel color which is suitable for use as a cracking variety.

*Storage and shipping quality.*—The present variety is not known to differ from other cultivars currently available in commerce.

*Resistance to disease.*—The present variety appears to be less susceptible to Walnut Blight than other commercially available cultivars such as 'Payne' and 'Ashley,' both of which are unpatented.

Although this new variety posesses the described characteristics noted above as a result of the growing conditions prevailing near stockton, Calif., it is to be understood that variations of the usual magnitude and characteristics incident to changes in growing conditions, fertilization, pruning and pest control are to be expected.

Having thus described and illustrated my new variety of walnut tree, what I claim is new and desire to secure by Plant Letters Patent is:

1. A new and distinct variety of walnut tree substantially as illustrated and described and what is somewhat similar to the 'Payne' walnut tree (unpatented), but which is distinguished therefrom and characterized principally as a novelty by producing a nut which is ripe for harvesting and shipment approximately September $14^{th}$ under the ecological conditions prevailing in Stockton, Calif., this date of harvesting is approximately 1 week later than the 'Payne' variety of walnut tree growing at the same geographical location.

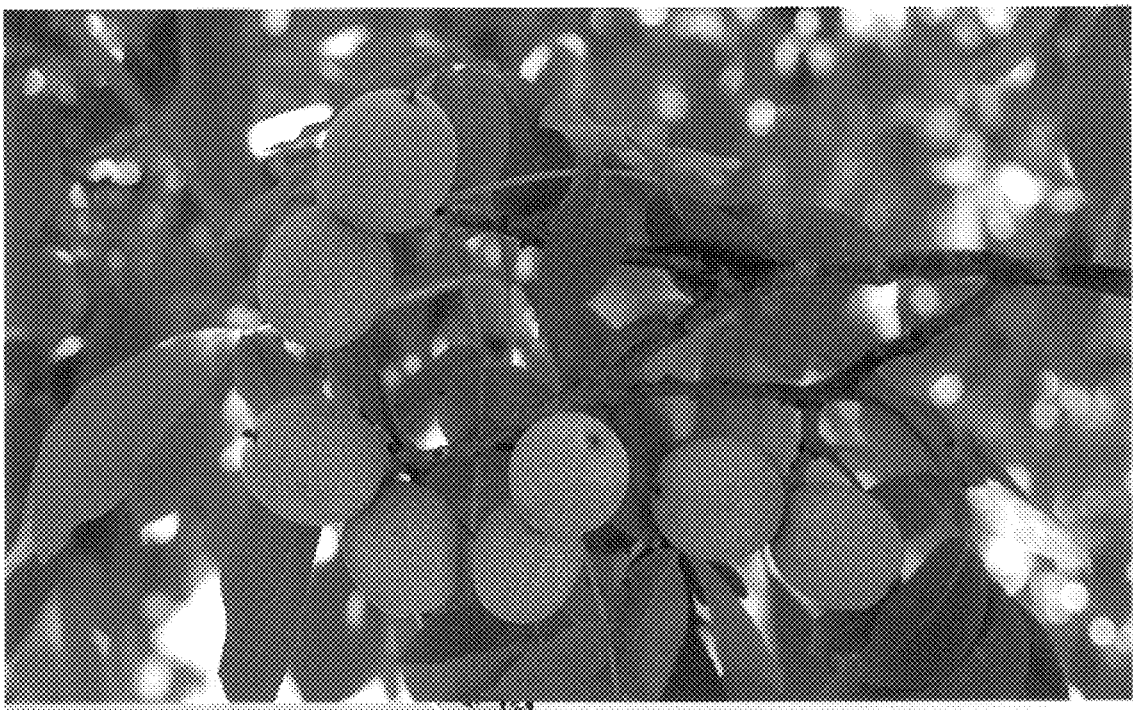
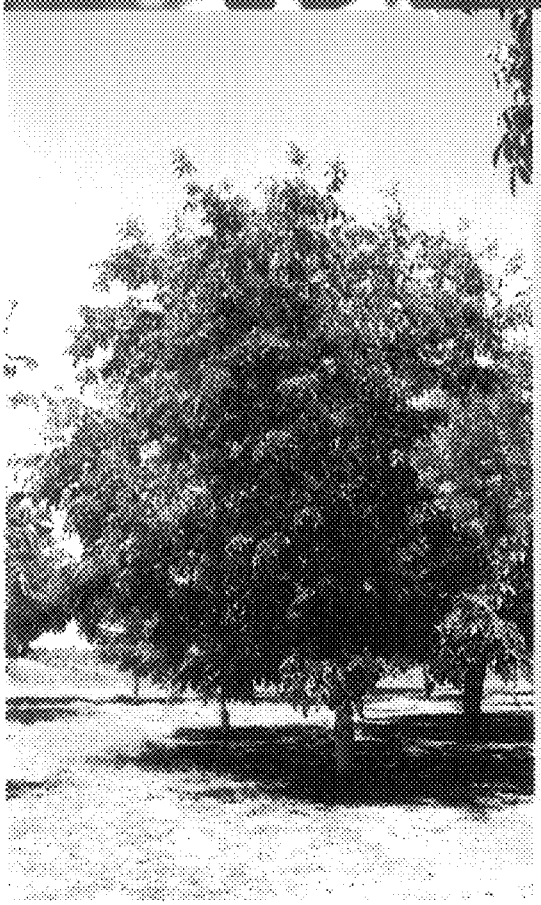
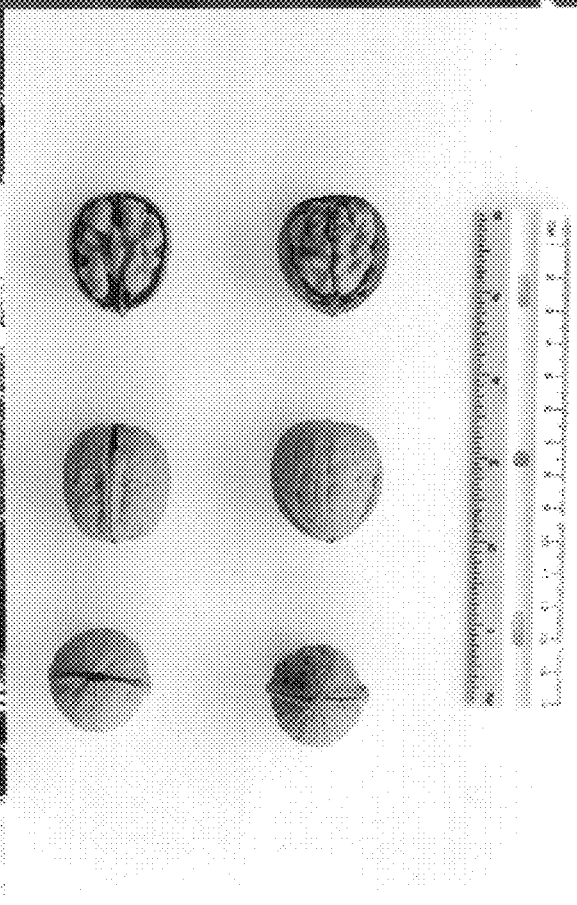

* * * * *